United States Patent
Robinson

(10) Patent No.: US 6,191,335 B1
(45) Date of Patent: Feb. 20, 2001

(54) DRESSINGS

(75) Inventor: Joseph William Robinson, Cambridge (GB)

(73) Assignee: Smith & Nephew PLC, London (GB)

(*) Notice: Under 35 U.S.C. 154(b), the term of this patent shall be extended for 0 days.

(21) Appl. No.: 09/341,880

(22) PCT Filed: Jan. 21, 1998

(86) PCT No.: PCT/GB98/00180
§ 371 Date: Sep. 13, 1999
§ 102(e) Date: Sep. 13, 1999

(87) PCT Pub. No.: WO98/31402
PCT Pub. Date: Jul. 23, 1998

(30) Foreign Application Priority Data

Jan. 21, 1997 (GB) .................................................. 9701178

(51) Int. Cl.[7] .................................................. A61F 13/00
(52) U.S. Cl. .................................. 602/41; 602/42; 602/43
(58) Field of Search .................................. 602/41, 43–46, 602/76, 77; 128/888, 889

(56) References Cited

U.S. PATENT DOCUMENTS 4,995,382 * 2/1991 Lang et al. .
5,563,233 * 10/1996 Reich et al. .

FOREIGN PATENT DOCUMENTS

WO 95/19795 * 7/1995 (WO) .
WO 96/01658 * 1/1996 (WO) .

* cited by examiner

Primary Examiner—Michael A. Brown
Assistant Examiner—Lalita Hamilton
(74) Attorney, Agent, or Firm—Larson & Taylor, PLC

(57) ABSTRACT

A wound dressing is provided which is made up of a backing layer, an apertured wound facing layer and an intermediate absorbent layer comprising fibers of material which upon contact with moisture will form a gel. The intermediate layer also includes a non-gel forming component, e.g., another fibrous material which can support the formed gels. The backing layer also has a water transmission rate which is greater than its moisture vapor transmission rate.

12 Claims, 1 Drawing Sheet

DRESSINGS

FIELD OF THE INVENTION

This invention relates to wound dressings and to methods of manufacture and the use thereof.

RELATED ART

Recently in wound developments dressings have been aimed at providing dressings which promote moist wound healing. Such dressings include, for example, that are sold by Smith & Nephew under the name ALLEVYN Adhesive (Trade Mark) and are described in European Patent Publication No. 0059049. Existing devices are essentially reservoirs for wound exudate, that is, they absorb exudate by means of an absorbent or hydrophilic material. Once the reservoir is saturated the dressing is generally changed. If such dressings are retained on the wound too long and dry out they are likely to adhere to the healing wound bed causing trauma, pain and delay in the wound healing process when they are removed There is therefore a need for a wound dressing which promotes moist wound healing but which does not rely solely on the physical process of absorption as a means of controlling exudate and the moist wound healing environment.

SUMMARY OF THE INVENTION

We have now found that such a dressing may be manufactured which employs both processes of absorption and moisture vapour transmission in conjunction. This is achieved by using a highly exudate absorbent reservoir in combination with a backing layer whose water transmission rate (WTR) is not less than its moisture vapour transmission rate (MVTR). The methods for measuring moisture vapour transmission rate (MVTR) and water transmission rate (WTR) which also described as inverted moisture vapour transmission rate are described in our European Patent Publication No. 0091800. As used herein both the WTR and MVTR transmission rates expressed in grams per square meter per 24 hours ($gm^{-2}$ 24 $hr^{-1}$) at 37° C. and the MVTR is measured at a relative humidity difference of from 10 to 100%.

Thus according to the invention we provide a dressing which comprises a backing layer and a wound facing layer and an absorbent layer intermediate the backing and wound facing layers characterised in that the backing layer has a water transmission rate (WTR) not less than its moisture vapour transmission rate (MVTR) and in that the absorbent layer is a fibrous layer comprising fibrous component which on absorbing moisture undergo a phase change to form a gel and a component which does not undergo a phase change to form a gel in the presence of moisture.

Preferably the WTR of the backing layer is great than its MVTR.

Suitably the backing layer is a thin film and may comprise any of those materials which are conventionally employed to form thin film surgical dressings. Suitable materials include those described in U.S. Pat. Nos. 4,595,001 and 4,747,401. Particularly apt materials are polyurethanes, for example polyester or polyether polyurethanes known as Estanes (Trade Mark). Other apt materials are elastomeric polyether polyesters, for example those known as Hytrels (Trade Mark) and polyether polyamides, for example those known as Pebaxes (Trade Mark). Other favoured materials include hydrophilic polymers such as hydrophilic polyurethanes including those described in UK Patent No.2093190B, especially the polyurethane described in Example 2 therein.

The backing layer may be moisture vapour permeable and may have a moisture vapour transmission rate of at least 500 $gm^{-2}$ 24 $hrs^{-1}$ suitably at least 1000 $gm^{-2}$ 24 $hrs^{-1}$, more suitably at least 1200 $gm^{-2}$ 24 $hrs^{-1}$ and preferably at least 1600 $gm^{-2}$ 24 $hrs^{-1}$ up to 5000 $gm^{-2}$ 24 hrs. Most preferably the MVTR should not be more than 3000 $gm^{-2}$ 24 $hrs^{-1}$.

The WTR of the backing layer may be at least 2000 $gm^{-2}$ 24 $hr^{-1}$, more suitably at least 3000 $gm^{-2}$ 24 $hr^{-1}$ and preferably at least 6000 $gm^{-2}$ 24 $hr^{-1}$ up to 20,000 $gm^{-2}$ 24 $hr^{-1}$.

The backing layer may have a thickness of from 15 to 100 $\mu m$, preferably 20 to 80 $\mu m$ and more preferably 25 to 50 $\mu m$, for example 27.5 $\mu m$, 30 $\mu m$, 35 $\mu m$, 40 $\mu m$.

The wound facing layer may comprise an apertured film or a net.

A preferred apertured film for use in the invention are those formed by a hot melt perforation process comprising the use of flames or hot gas.

Preferred apertured films for use in the invention are in the form of flexible polymer nets. A polymer net is used herein as a polymer sheet having apertures defined by integral strands and junctures. Such nets may be formed by stretching films or sheets embossed with thinner areas.

Any conventionally known material may be used, but favoured polymer nets comprise an elastomeric polymer and in particular a thermoplastic elastomeric polymer.

Such nets of elastomeric polymer can impart 'softness' to the surface of the device of the invention.

Suitable thermoplastic elastomeric polymers include polyether ester and polyether-polyamide block copolymers, polyurethanes, styrene-butadiene and styreneisoprene block copolymers, polyisobutadiene and ethylene-vinyl acetate copolymers.

Nets for use in the invention may comprise a blend of elastomeric polymer such as ethylene vinyl acetate copolymer with a compatible polymer or an incompatible polymer such as polyolefine, for example low density polyethylene or polystyrene.

Suitable nets for use in the invention which comprise a blend of ethylene vinyl acetate and an incompatible polymer are disclosed in European Patent No.141592.

The intermediate absorbent layer may comprise any conventionally known absorbent materials. Preferably, the absorbent layer will provide resistance to, e.g. high molecular weight materials, such as proteins, polysaccharides etc., which might tend to effect the WTR of the backing layer when the wound is highly exuding. Thus the gelling component of the absorbent layer may comprise a superabsorbent material which gels when wet. Suitable superabsorbent hydrogels are described in U.S. Pat. Nos. 3,669,103 and 3,670,737. Within the scope of such hydrogels it is intended to include, e.g. alginate and/or other hydrocolloids. A preferred superabsorber is polyacrylic acid an example of which is that known as OASIS fibres (Technical Absorbents). The gelling component of the absorbent layer will be a fibrous or filamentary material.

The non-gelling component of the absorbent layer may comprise fibrous constituents which are non-absorbent or sparingly absorbent. When the composite comprises two fibrous components then it is preferred that one constituent will be a superabsorber as hereinbefore described and the other will be non-absorbent or sparingly absorbent to exudate.

The fibrous components of the absorbent layer may be present in amount of from 130 gm$^{-2}$ to 300 gm$^{-2}$, preferably from 100 to 175 gm$^{-2}$.

The size and shape of the fibres used may vary according to, inter alia, that nature of the fibrous material and the degree of absorption/transmission desired in the article. Nevertheless, fibres which are substantially linear are preferred. The diameter of such fibres would be similar to that conventionally used in absorbent articles and/or dressings. Substantially linear fibres may be of conventional lengths used in the art. Preferred substantially linear fibres are from 5 to 50 mm long, preferably from 10 to 20 mm long.

The non-gelling fibrous components may comprise one or more fibrous materials. The fibrous material in the composite may comprise any conventionally known fibres including natural or synthetic materials. For example, a fibrous component may comprise a cellulosic fibre or a composite of a cellulosic fibre and a thermobonding fibre. Examples of cellulosic fibre include, but are not limited to cotton fibres or wood pulp fibres. Thermobonding fibres include, for example, Danaklon ESC.

The use of non-gelling fibrous components in the composite absorbent layer may be advantageous in that they may provide support for the superabsorber fibres, particularly when the superabsorber becomes a gel as it becomes wet; such non-gelling fibres may provide improved wicking of exudate away from the wound facing layer to the backing layer; and it may provide a physical barrier to high molecular weight exudate debris which could otherwise reduce the efficiency of the backing layer.

Thus a preferred absorbent layer would comprise a superabsorber, e.g. polyacrylic acid; a cellulosic fibre, e.g. cotton fibre or wood pulp; and a thermobonding fibre, e.g. Danaklon ESC. In such an absorbent layer the components would be uniformly dispersed and then formed into, e.g. a web of absorbent material.

The dressings of the invention may comprise an adhesive layer on the body facing surface of the wound contact layer. In that case, any conventionally known pressure sensitive adhesives may be used.

In a preferred embodiment the edges of the dressing are preferably sealed, such that the absorbent layer is housed in a compartment which prevents, eg. exudate and/or fibres from being lost at the edges of the dressing. Thus, for example, the edges of the backing layer may be bonded to the wound facing layer. The layers may be adhesively bonded or thermally bonded.

The use of a fibre supported superabsorber is novel per se. Thus according to a further feature of the invention we provide the use of a fibre supported superabsorber in the manufacture of a dressing as hereinbefore described.

According to a further aspect of the invention we provide a process for the manufacture of an absorbent article as hereinbefore described which comprises;

combining the absorbent layer components to produce a web and subsequently bonding the web; and bonding the web, the backing layer and wound facing layer.

The process is preferably carried out under an appropriately humidity controlled atmosphere.

The absorbent layer may be manufactured by combining the components, including at least one fibrous component, in an air laid web using commercially available equipment, e.g. a Rando pre feeder, an opener blender, a feeder and a webber. The web can then be bonded, either by heat bonding, chemical bonding or by needle punching.

The manufactured absorbent layer can then be bonded to the backing layer and wound facing layer. The bonding may include chemical bonding but is preferably thermally bonded by heat lamination.

The absorbent articles may then be sent to size using conventional processes known per se.

The dressings of the invention are useful if wound healing and especially moist wound healing. Thus dressings of the invention are indicated in the treatment or alleviation of, inter alia, pressure sores, leg ulcers, cuts and abrasions and exuding wounds.

According to a yet further feature of the invention we provide a method of wound healing which comprises the application of a dressing as hereinbefore described to the wound of a patient.

BRIEF DESCRIPTION OF THE DRAWINGS

The invention will now be described by way of example only and with reference to the accompanying drawing, which is a cross-sectional view of a dressing of the invention.

DESCRIPTION OF A PREFERRED EMBODIMENT

Figure 1:
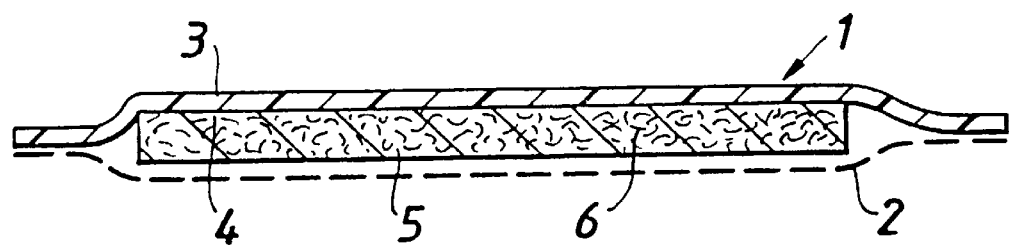

Referring to the drawing, a dressing (1) comprises a wound facing layer (2), in the form of a net or an apertured film for example the polyurethane net utilised as the wound contact layer described in the Examples of European Patent Publication No. 0059049; a backing layer (3) for example the hydrophilic polyurethane base film described in the examples of European Patent Publication No. 0091800 and an intermediate layer (4) which comprises a polyacrylic acid based superabsorber material (5) and a cotton fibre support material (6).

In use the dressing may be applied to the wound site of a patient and adhered with tape or, optionally, the wound facing layer (2) may be provided with a body facing adhesive layer.

What is claimed is:

1. A wound dressing comprising a backing film, an apertured wound facing layer and an absorbent layer intermediate the backing film and wound facing layer, the backing film having a water transmission rate greater than the moisture vapour transmission rate thereof and the absorbent layer comprising a fibrous layer comprising a fibrous component which, on absorbing moisture, undergoes a phase change to form a gel and a component which does not undergo a phase change to form a gel in the presence of water, the water transmission rate of the backing film being at least 4000 gm$^{-2}$ 24 hr$^{-1}$ at 37° C. and the moisture vapour transmission rate of the backing film being at least 1000 to 3000 gm$^{-2}$ 24 hr$^{-1}$ at 37° C. and a relative humidity difference of from 10 to 100%.

2. A dressing as claimed in claim 1 wherein the backing film is an elastomeric polymer.

3. A dressing as claimed in claim 1 wherein the backing film has a thickness of from 15 to 100 μm.

4. A dressing as claimed in claim 1 wherein the wound facing layer comprises an elastomeric polymer apertured film or net.

5. A dressing as claimed in claim 1 wherein the elastomeric polymer is a polyether ester, a polyether-polyamide block copolymer, a polyurethane, a styrene-butadiene or styrene-isoprene block copolymer, polyisobutadiene or a ethylene-vinyl acetate copolymer or mixtures or blends thereof.

6. A dressing as claimed in claim 1 wherein the absorbent layer comprises fibres of a density of from 130 to 300 gm$^{-2}$.

7. A dressing as claimed in claim 1 wherein the gelling component of the absorbent layer comprises fibres of polyacrylic acid or an alginate.

8. A dressing as claimed in claim 1 wherein the non-gelling component is a fibrous material.

9. A dressing as claimed in claim 8 wherein the non-gelling fibrous material is sparingly or substantially non-absorbent.

10. A dressing as claimed in claim 1 wherein the non-gelling component of the absorbent layer comprises cellulosic fibres.

11. A dressing as claimed in claim 1 wherein the backing and wound facing layers are sealed together at the edges of the dressing.

12. A dressing as claimed in claim 1 wherein the wound facing surface of the wound facing layer carries a layer of a skin-friendly pressure sensitive adhesive.

* * * * *